United States Patent [19]

Nakamura et al.

[11] Patent Number: 5,674,696
[45] Date of Patent: Oct. 7, 1997

[54] APPARATUS FOR THE DETERMINATION OF A TRACE AMOUNT OF AN ANALYTE SUBSTANCE OR ORGANISM

[75] Inventors: Michihiro Nakamura; Satomi Matsui; Keiko Oka; Hitoshi Tsuruta, all of Kurashiki, Japan

[73] Assignee: Biosensor Laboratories Co., Ltd., Tokyo-to, Japan

[21] Appl. No.: 328,057

[22] Filed: Oct. 24, 1994

[30] Foreign Application Priority Data

Nov. 1, 1993 [JP] Japan .................. 5-273573

[51] Int. Cl.$^6$ ............ G01N 33/543; G01N 33/569; G01N 27/327
[52] U.S. Cl. ............ 435/7.32; 204/193; 204/194; 204/400; 204/403; 422/82.01; 422/82.03; 435/7.2; 435/7.21; 435/29; 435/174; 435/176; 435/287.1; 435/287.2; 435/288.1; 435/817; 436/163; 436/518; 436/528; 436/531; 436/806
[58] Field of Search ................ 422/62, 68.1, 69, 422/82.01, 82.03, 119; 435/7.1, 7.2, 7.21, 7.24, 7.32, 7.4, 29, 174, 176, 177, 287, 288, 817, 287.1, 287.2, 288.1; 436/518, 528, 531, 68, 163, 806; 204/193, 194, 400, 403

[56] References Cited

U.S. PATENT DOCUMENTS

| 4,402,819 | 9/1983 | Rechnitz et al. ............ 204/418 |
| 4,592,994 | 6/1986 | Mattiasson ............ 435/7 |
| 5,059,522 | 10/1991 | Wayne ............ 435/7.2 |
| 5,066,582 | 11/1991 | Tsuruta et al. ............ 435/7.1 |
| 5,116,759 | 5/1992 | Klainer et al. ............ 435/288 |

FOREIGN PATENT DOCUMENTS

| 0 329 458 | 8/1989 | European Pat. Off. . |
| 0 333 253 | 9/1989 | European Pat. Off. . |

*Primary Examiner*—Christopher L. Chin
*Attorney, Agent, or Firm*—Jones, Tullar & Cooper, P.C.

[57] ABSTRACT

There is disclosed an apparatus for the determination of a trace amount of an analyte substance or organism. A substrate solution is brought into contact with a small diameter tube which has captured, at least on its inner surface, a trace amount of an analyte substance or organism. The trace amount has the ability to change the pH of the substrate solution. A pH change following a reaction of a substrate in the substrate solution in the small diameter tube is measured;

the apparatus has a cuvette having an inlet and an outlet for the substrate solution, a pH electrode accomodated in the cuvette, a pump for supplying the substrate solution in the cuvette, a positioning structure for positioning, in the cuvette, the small diameter tube with the pH sensitive plane of the pH electrode and spacing the surface and the plane at 1 mm or below from each other, and a sealing structure for maintaining a formed by the outer surface of the small diameter tube accomodated in the cuvette and the inner surface of the cuvette at liquid tight condition.

3 Claims, 5 Drawing Sheets

1

APPARATUS FOR THE DETERMINATION OF A TRACE AMOUNT OF AN ANALYTE SUBSTANCE OR ORGANISM

FIELD OF THE INVENTION

The present invention relates to an apparatus for the determination of a trace amount of an analyte substance or organism. More particularly, the present invention relates to an apparatus for quantitative determination of a particular substance or organism contained in a very small amount in the multicomponent system such as a living body sample, by utilizing a pH change of a substrate solution resulting from the physiological activity of an analyte substance or organism to be determined. The apparatus of the present invention can be applied to a wide range of fields such as fundamental medicine, veterinary medicine, biochemistry, pharmacology and the like in addition to the determination of a trace amount of living body substances in clinical tests.

BACKGROUND OF THE INVENTION

Substances responsible for the physiological activity of a living body are generally present in a very small amount, and many of them play an important role on the living body. Since it is therefore important in the organism-related fields such as medicine, biochemistry and the like to quantitatively determine a trace amount of physiologically active substances, a variety of methods have been proposed and put to practical use. For example, for determining an enzyme which is one of the physiologically active substances, there is generally employed a method of determination according to which an enzyme reacts with a corresponding substrate contained in a substrate solution and a change in the optical properties of the substrate solution is measured.

In addition, since an organism such as a cell, microorganism and the like has also a physiological activity, it is important in the above organism-related fields to quantitatively determine the organism as in the case of the above physiologically active substances. As examples of a method for determining a cell among such an organism, there are frequently employed a method for culturing cells and observing the cultured cells using an electron microscope, a flow cytometry method and a rosette method [see "Saibo Meneki Kino Kensa no Subete (All About Cellular Immunofunction Assay)", edited by monthly Medical Technology, Ishiyaku Press (1985)]. Recently, a detecting method using a gene has been actively employed [see, for example, "PCR Jikken Manual (PCR Experimental Manual)", translated under the supervision of Takashi Saito, HBJ Press (1991)]. On the other hand, for determining the microorganism, a detecting method using a gene has recently been used in addition to a conventional method employing observations using a microscope. However, all of these methods require skill and complicated operations as well as expensive apparatus for determination.

A method has been proposed according to which the determination of a trace amount of an analyte substance is made by bringing, after completion of an analyte-receptor reaction, a solid phase into contact with a substrate solution and measuring the pH change of the substrate solution following the degradative reaction of the substrate in the solution. The above solid phase is confronted with a pH sensitive plane of a pH electrode for measuring a pH change of the substrate solution so as to space a gap between the solid phase and the plane at 1 mm or less, and then the pH change of the substrate solution present in the gap is measured. An apparatus for carrying out the method is also proposed see [JP-A 1-212347].

The above apparatus is premised on heterogenous EIA, so-called ELISA (Enzyme Linked Immuno Sorbent Assay), and is employed for determining mainly an analyte substance which itself has no "ability to change pH of a substrate solution" (referred to hereinafter as "pH change inducible ability"). Therefore, after the first immunoreaction is carried out between the solid phase and an analyte to capture the analyte substance on the surface of the solid phase, a second immunoreaction must be done by binding the second receptor labelled with an enzyme having the pH change inducible ability, such as urease and the like, to the analyte captured on the surface of the solid phase (sandwich method), or by reacting an analyte labelled with an enzyme having the pH change inducible ability with the solid phase (competitive method). That is, in the apparatus for ELISA, a series of operations including the first immunoreaction—the first washing—the second immunoreaction—the second washing—measurement of a pH change are required. Therefore, the operations are complicated and automation of all of these operations necessarily needs a large-scale apparatus.

On the other hand, in the case where a subject to be determined is a substance or organism having itself the pH change inducible ability such as an enzyme, a cell, a microorganism and the like, binding of the second receptor labelled with an enzyme having the pH change inducible ability, such as urease and the like, to an analyte substance to be determined is not necessarily required and, instead of it, a pH change of a substrate solution may be measured after an analyte substance or organism is captured on the surface of the solid phase and washing is carried out.

OBJECTS AND SUMMARY OF THE INVENTION

The main object of the present invention is to provide a simplified apparatus which can determine a trace amount of an analyte or organism having a pH change inducible ability by simple operations so that washing of the solid phase after capture of an analyte substance or organism thereon and measurement of a pH change of a substrate solution can be carried out in the same cuvette.

SUMMARY OF THE INVENTION

According to the present invention, there is provided an apparatus for the determination of a trace amount of an analyte substance or organism by bringing a substrate solution into contact with a small diameter tube which has captured, at least on its inner surface, a trace amount of an analyte substance or organism having an ability to change pH of the substrate solution and measuring a pH change following a reaction of the substrate in the substrate solution in the small diameter tube. The apparatus includes:

a cuvette having an inlet and outlet for the substrate solution, a pH electrode accommodated in the cuvette, pumping means for supplying the substrate solution in the cuvette, positioning means for positioning, in the cuvette, the small diameter tube which has captured, at least on its inner surface, the analyte substance or organism, to be determined, having an ability to change pH of the substrate solution so as to confront the inner surface of the small diameter tube with the pH sensitive plane of the pH electrode and space the surface and the plane at 1 mm or less from each other, and a sealing means for maintaining a space formed by the outer surface of the small diameter tube accommodated in the cuvette and the inner surface of the cuvette at a liquid tight condition.

The present invention will become apparent to those skilled in the art from the following description with reference to the accompanying drawings.

DETAILED DESCRIPTION OF THE INVENTION

Since, in the apparatus of the present invention, a substrate solution is brought into contact with a small diameter tube which has captured a trace amount of an analyte substance or organism having a pH change inducible ability and a pH change following a reaction of the substrate in the substrate solution is measured, a trace amount of an analyte substance or organism, to be determined, having the pH change inducible ability can be determined to a high degree.

As used herein, a reaction of a substrate refers to various reactions such as degradation, oxidation, reduction, rearrangement, hydrolysis, elimination, isomerization, polymerization and the like of the substrate by the enzyme and the like as well as the metabolism of the substrate by the organism. Since, in the apparatus of the present invention, a space formed by the outer surface of the small diameter tube accommodated in the cuvette and the inner surface of the cuvette is sealed to liquid tight condition and a substrate solution supplied by pumping means in the cuvette flows through the interior of the small diameter tube, the interior of the small diameter tube is automatically washed with the substrate solution. Thus, washing of the interior of the small diameter tube and measurement of a pH change can be carried out in one cuvette and, therefore, the apparatus for determination is simplified and measurement operations are also simplified.

The apparatus of the present invention is explained below by referring to the attached drawings.

Figure 1:
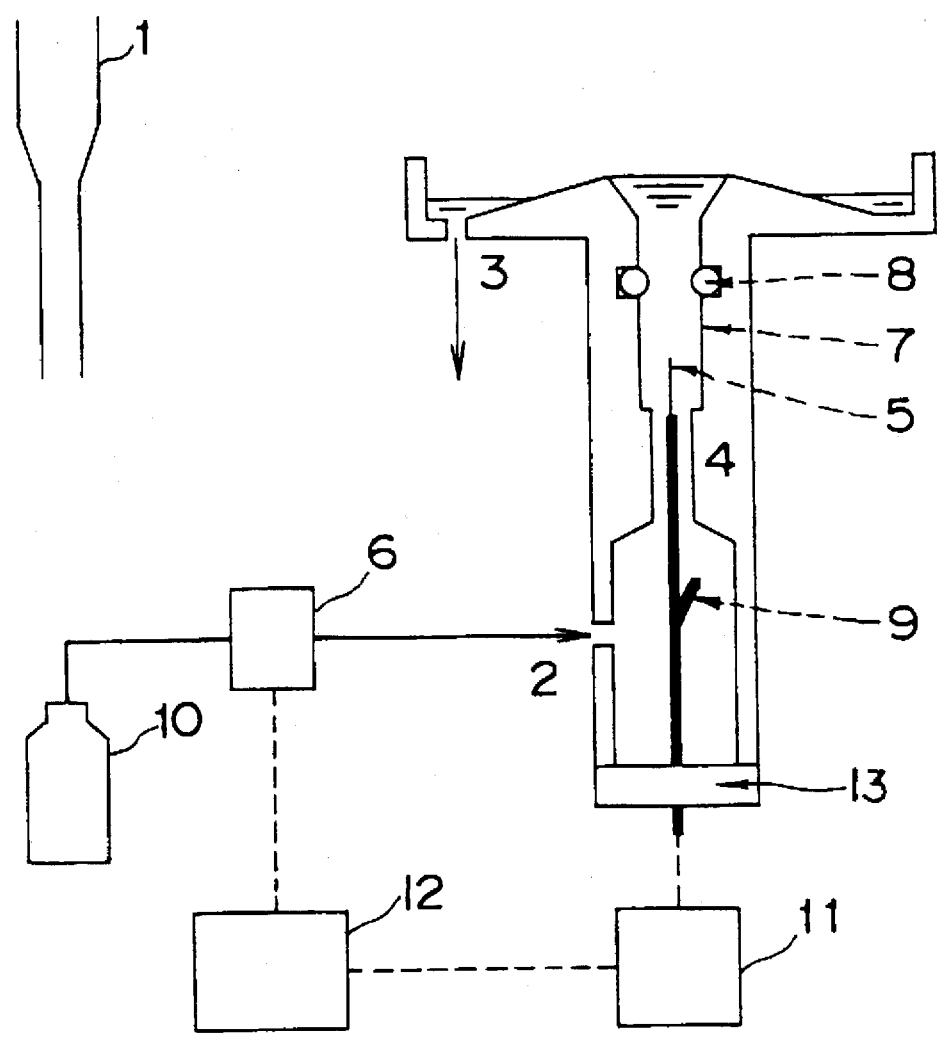
FIG. 1 is a schematic illustration showing a first embodiment of the apparatus of the present invention.

FIG. 1 shows the outline of one embodiment of the apparatus of the present invention. As shown in FIG. 1, the apparatus of the present invention comprises a cuvette 4 having an inlet 2 and outlet 3 for a substrate solution, a pH electrode 5 accommodated in the cuvette 4, pumping means 6 for supplying a substrate solution in the cuvette 4, positioning means 7 for positioning, in the cuvette 4, a small diameter tube 1 which has captured, at least on its inner surface, an analyte substance or organism, to be determined, the analyte substance having an ability to change the pH of the substrate solution so as to confront the inner surface of the small diameter tube 1 with the pH sensitive plane of the pH electrode and space the surface and the plane at 1 mm or less from each other, and a sealing means 8 for maintaining a space formed by the outer surface of the small diameter tube 1 accommodated in the cuvette and the inner surface of the cuvette 4 at a liquid tight condition. Reference numeral 9 represents a reference electrode, 10 represents a liquid reservoir for pooling a substrate solution, 11 represents a circuit for activating the pH electrode, and 12 represents a means for controlling the action of the pump and reading and displaying the signal from the pH electrode.

The cuvette 4 has large cylindrical diameter portions at its upper and lower part and a small diameter portion at its intermediate part, and both ends of the large diameter portions are open. The lower large diameter portion is provided with the inlet 2 for the substrate solution and the upper large diameter portion is provided with the outlet 3 for the substrate solution. The lower end opening of the cuvette 4 is closed by an electrically insulating resin (13) for accommodating the pH electrode 5 and the reference electrode (9) in the cuvette at a liquid tight condition. The cuvette 4 may be made of plastic, metal, inorganic glass or the like.

As the pH electrode 5 accommodated in the above cuvette 4, various pH microelectrodes, for example, a pH sensitive field-effect transistor (referred to as "pH-FET" hereinafter), a surface metal oxide type pH electrode such as a palladium oxide/palladium wire, and a coated wire type pH electrode made by coating a pH sensitive polymer membrane containing a proton acceptor on the metal wire or carbon wire can be used in addition to a glass electrode which has been previously used most frequently. However, the glass electrode type pH electrode has a tendency to increase induced noises as the diameter is reduced. Although the surface metal oxide wire type pH electrode is easy to be reduced in diameter, it has defects in terms of long-term life in water and the like. Although the coated wire type pH electrode is also easy to be reduced in diameter, it has such defects that the linear region responsive to a pH change is narrow and life in water is short. For these reasons, the above problems must be solved beforehand in order to employ the above pH electrodes.

On the other hand, the pH-FET has excellent characteristics such as: (1) it is easy to be reduced in diameter; (2) it has small induced noises when reduced in diameter; (3) since it is prepared by IC techniques, the scatter of properties between electrodes can be made small and its pH sensitive plane (gate part) can be made very small; (4) it has an extremely rapid response to a pH change and has no remnant hysterisis in the response curve; (5) it has a wide linear region responsive to a pH change; and (6) it has a semipermanent life when stored in water and small change in properties such as the pH sensitivity over a period of time. Therefore, the pH-FET is most suitable for a pH electrode employed in the present apparatus. As the pH-FET, some types such as the (1) entirely circumferentially insulated type (see JP-B 57-43863), (2) the pn-junction-separated type (see JU-B 58-5245), (3) the SOS type (see JP-A 59-48646) and the like are known. Any of the above types can be used in the present invention provided that its structure must satisfy the following requirements: (1) it has a pH sensitive plane near its tip; (2) a tip part of an elemental device containing the pH sensitive plane has a thickness that can be inserted in a small diameter tube which has captured thereon a subject to be determined; (3) a tip part of the elemental device is 1 to 10 mm in length, preferably 1 to 3 mm; (4) all of the upper, lower and side planes of the tip part of the elemental device are electrically insulated from an outer solution.

The diameter of the tip of the elemental device is desirably such that the tip can be inserted in a small diameter tube having the inner diameter of 2.0 mm or less, normally 0.8 mm or less. For example, when the inner diameter of the small diameter tube is 0.55 mm, it is sufficient that the width of the tip of the elemental device is 0.45 mm or below and the thickness is 0.20 mm or below. When the length of the tip of the elemental device is greater 10 mm, such problems arise that the tip becomes easy to break and the necessary length of the small diameter tube for capturing an analyte substance or organism to be determined becomes longer. When the length is below 1 mm, the length of the tip of the elemental device to be inserted in the small diameter tube becomes too short and, for that reason, a reaction of a substrate in the small diameter tube is easily influenced by a solution outside of the small diameter tube.

It is desirable that the pH-FET employed in the present invention has a pH sensitivity of 40 to 60 mV/pH, preferably 50 to 60 mV/pH at 25° C. As the pH sensitive membrane, materials having excellent stability in water such as silicon nitride, aluminium oxide, tantalum oxide and the like are desirably used. In particular, tantalum oxide and aluminium oxide are excellent in stability in water and pH responsive properties and the like. The pH-FET having tantalum oxide as the pH sensitive membrane is suitable for a pH electrode employed in the present invention.

For determining a trace amount of an analyte or organism having the pH change inducible ability using the present apparatus, the pH-FET having an extremely low level of noises (normally 0.05 mV or below at not higher than constant pH) is preferably used. For this purpose, the pH-FET having not lower than 50 microgiemens, preferably not lower than 100 microgiemens, more preferably not lower than 200 microgiemens of the mutual conductance is desirably used. It is desirable that the leakage current is not higher than 30 nA, preferably not higher than 10 nA when 3 V of the voltage is applied between a source electrode of the pH-FET and an outer electrode while soaking the tip part of the elemental device of the pH-FET and an outer electrode in a physiological sodium chloride solution. When the mutual conductance is below 50 microgiemens or the above leakage current is above 30 nA, the noises at measurement grow larger.

As the reference electrode 9, liquid-junction type reference electrodes such as a saturated calomel electrode, a silver-silver chloride electrode and the like, field-effect transistors having an ion-insensitive membrane as a gate membrane (JP-B 58-25221), coated wire type reference electrodes obtained by coating an ion-insensitive membrane on a metal wire or carbon wire can be used. Although any type of reference electrodes may be used in the present apparatus, liquid-junction type reference electrodes have the highest reliance at this point and are preferably used. Preferably, the reference electrode is provided, in the cuvette 4, at the lower large portion thereof which has a liquid-junction with a pH sensitive plane of the pH electrode as shown in FIG. 1. The reference electrode 9 may be provided at any place which has a liquid-junction with the pH sensitive plane of the pH electrode, for example, at a place outside of the cuvette 4 such as a place between the pumping means 6 and an inlet 2 of the cuvette 4.

As the pumping means 6 for supplying a substrate solution in the cuvette 4, any pumping means which can provide a supplying rate of 5 to 1000 ml/h are employed. For example, known pumps such as a perista pump, a syringe pump and the like can be employed without particular limitations.

As the positioning means for positioning the small diameter tube 1, known means for adjusting a gap between the inner surface of the small diameter tube 1 and the pH sensitive plane of the pH electrode 5 can be used. For example, the small diameter tube 1 may be movable in the direction of its diameter, or as shown in FIG. 1, the upper large diameter portion of the cuvette 4 may be a guide for the small diameter tube 1. Using the above means for positioning the small diameter tube, a distance between the inner surface of the small diameter tube 1 and the pH sensitive plane of the pH electrode is adjusted to 1.0 mm or below, preferably 0.5 mm or below. When a distance between the inner surface of the small diameter tube and the pH sensitive plane becomes above 1.0 mm, since the pH changing rate of a substrate solution sealed in a gap between the inner surface of the small diameter tube 1 and the pH sensitive plane is decreased rapidly, the high sensitivity can not be actually obtained.

As the sealing means 8 for maintaining a space formed by an outer wall surface of the small diameter tube 1 accommodated in the cuvette and the inner surface of the cuvette 4 at liquid tight condition, any means having the function to maintain the above space at liquid tight condition can be used. Normally, an O ring or taper is used.

The small diameter tube 1 is required to have a length that at least pH sensitive plane of the pH electrode is sufficiently inserted therein. For example, when the pH sensitive plane of the pH electrode is 1.5 mm in length, the length of a portion in the small diameter tube 1 necessary for capturing an analyte substance or organism to be determined is normally 3 mm or greater. The shape of the small diameter tube as a whole may be any one in which the portion for capturing an analyte substance or organism to be determined is satisfied with the above requirements. The pipette tip-like shape composed of the small diameter portion and the large diameter portion may be used.

The small diameter tube 1 may be made of polyolefin polymer such as polystyrene, polyethylene, polypropylene, polytetrafluoroethylene, polyvinyl chloride, polymethyl methacrylate, polyvinyl alcohol, ethylene-vinyl alcohol copolymer and the like, polyester polymer such as polyethylene terephthalate, polybutylene terephthalate and the like, polysiloxane polymer such as poly(dimethylsiloxane) and the like, polyamide polymer such as nylon 6, nylon 6.6 and the like, polycarbonate, cellulose polymer such as cellulose acetate, nitrocellulose and the like, as well as various inorganic glasses.

It is required that the small diameter tube 1 can capture, at least on its inner surface, a trace amount of an analyte or organism having the pH change inducible ability. As a means for endowing the small diameter tube 1 made of the above material with an ability to capture a trace amount of the above analyte substance or organism to be determined, known means can be used. For example, for capturing a protein molecule such as enzyme, an antibody reacting with the protein molecule is immobilized at least on the inner surface of the small diameter tube 1 as a receptor for the protein molecule and, thereafter, a blocking agent such as bovine serum albumin or the like is adsorbed thereon. In addition, other known methods in the enzyme immunoassay field can be conveniently used [see, for example, "Enzyme Immunoassay", third edition, Ishikawa et al., Igakushoin Press (1987)].

On the other hand, for an such as a cell, a microorganism and the like, an antibody reacting with various proteins exposed on the surface of the organism, a ligand molecule reacting with various receptors exposed on the surface of the organism or partial peptide thereof, or a receptor reacting with various cell adhesion factors exposed on the surface of the organism or partial peptide thereof is immobilized at least on the inner surface of the small diameter tube 1 and blocking is carried out as described above.

A subject to be determined by the present apparatus is an analyte substance or organism having the pH change inducible ability. Examples of such a substance or organism are enzyme, cell, microorganism, and organelle such as mitochondria and the like.

A substrate solution to be supplied in the cuvette is selected depending upon an analyte or organism to be determined. For example, for determining an enzyme, a solution containing a substrate to induce the pH change in response to the enzyme's action is used as the substrate solution. Examples of a combination of an enzyme and a substrate are alcohol dehydrogenase/alcohol, glucose oxidase/glucose, catechol oxidase/catechol, NADH peroxidase/NADH, lipase/triacylglycerol, acetylesterase/ acetic ester, acetylcholinesterase/acetylcholine, gluconolactonase/gluconolactone, alkaline phosphatase/p-nitrophenolphosphoric acid, allylsulfatase/allyl sulfate, urease/urea and the like.

For determining an organism such as a cell, a microorganism or the like, a culture solution containing a substrate which can induce a pH change by metabolism by the organism may be used as the substrate solution. As the substrate, sugars such as glucose, fructose, sucrose and the like are most generally used. In this case, a culture solution having the weak buffering ability is preferably used so as to sharply change the pH by metabolism by the organism.

Figure 3:
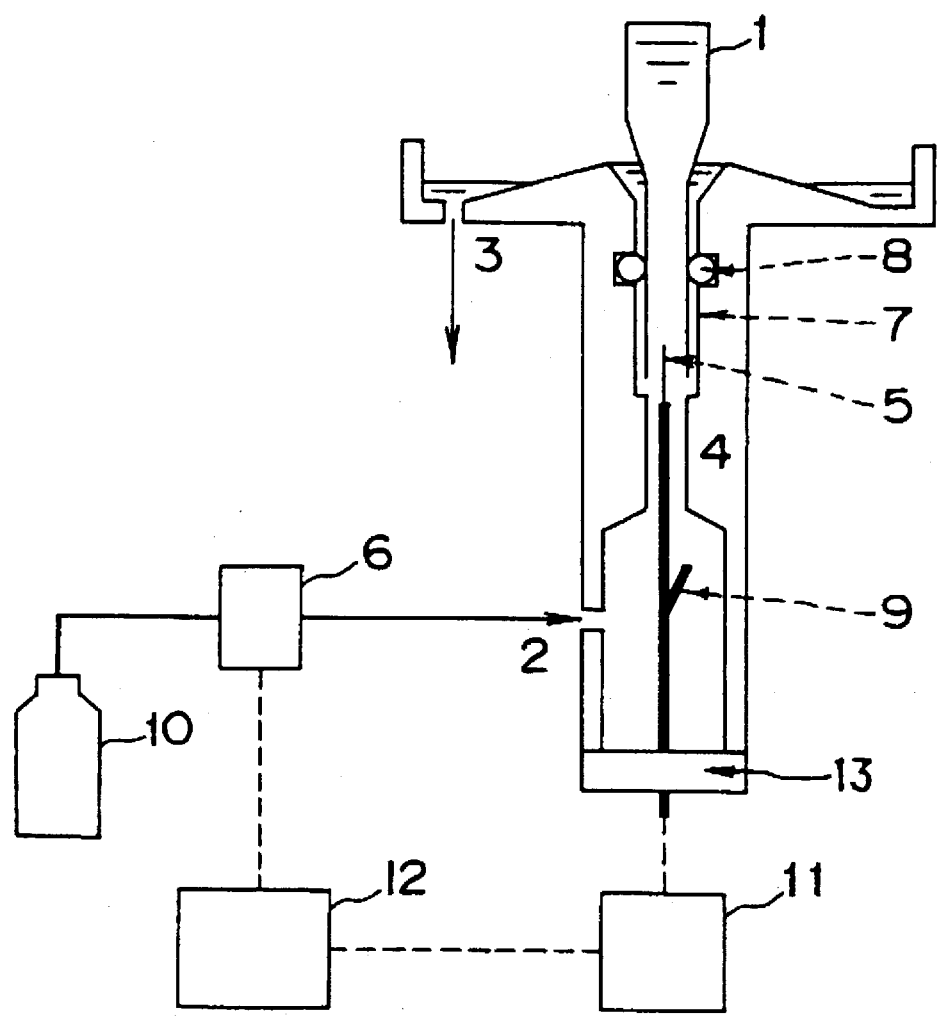
FIG. 3 is a view showing the apparatus of the present invention when a measurement is being carried out.

A method for determination employing the present apparatus is explained by referring to FIG. 3.

A sample solution is first sucked in the tip part of the small diameter tube 1 which can capture thereon a substance or organism having the pH change inducible ability and allowed to stand for a constant period of time. By this operation, an analyte substance or organism, to be determined, having the pH change inducible ability is captured in the inner surface of the small diameter tube 1. Alternatively, the tip part of the small diameter tube 1 may be soaked in a sample solution and incubated for a constant period of time so as to capture an analyte substance or organism, to be determined, having the pH change inducible ability on the inner surface of the small diameter tube 1.

Then, the small diameter tube 1 which has captured, on its inner surface, an analyte substance or organism having the pH change inducible ability as described above is inserted manually in the cuvette 4 through an upper end opening of the cuvette 4 so that the inner surface of the small diameter tube 1 completely surrounds the pH sensitive plane of the pH electrode. As a result, a space formed by the outer surface of the small diameter tube 1 inserted in the cuvette 4 and the inner surface of the cuvette 4 is sealed in a liquid tight condition by the sealing means 8. Alternatively, an operation of insertion of the small diameter tube 1 in the cuvette may be automated by separately disposing a means for accommodating the small diameter tube. As the means for accommodating the small diameter tube, for example, known means such as the means described in JP-A 1-212347 can be used.

With the small diameter tube 1 accommodated in the cuvette 4 as described above, a substrate solution is supplied in the cuvette 4 from a liquid reservoir (10) by the supplying pump 6. The substrate solution supplied in the cuvette 4 flows from the lower to the upper part in the small diameter tube 1 and is discharged through the outlet 3 of the cuvette 4. Thus, the interior of the small diameter tube 1 is automatically washed with the substrate solution. Upon this washing of the interior of the small diameter tube, a reaction of a substrate in the substrate solution occurs in the small diameter tube and a pH change of the substrate solution proceeds. However, this pH change can be made approximately zero by maintaining the substrate solution supplying rate sufficiently high. In addition, insertion of the small diameter tube 1 in the cuvette 4 and washing of the interior of the small diameter tube may be conveniently carried out as a series operations when the small diameter tube 1 is inserted in the cuvette 4 while supplying a substrate solution in the cuvette 4 from a liquid reservoir 10 by the supplying pump means 6.

When the substrate solution is sufficiently supplied and washing of the interior of the small diameter tube 1 is completed, supplying of the solution is stopped. Thereafter, a pH change of the substrate solution in the small diameter tube 1 following a reaction of the substrate in the substrate solution is measured. From the pH change, the concentration of an analyte substance or organism to be determined in a sample solution can be obtained.

After measurement is completed, the small diameter tube 1 is pulled out from the cuvette 4 and a substrate solution is supplied again in the cuvette 4 from the liquid reservoir 10 by the supplying pump means 6. Thus, the interior of the cuvette 4 is automatically washed.

Figure 2:
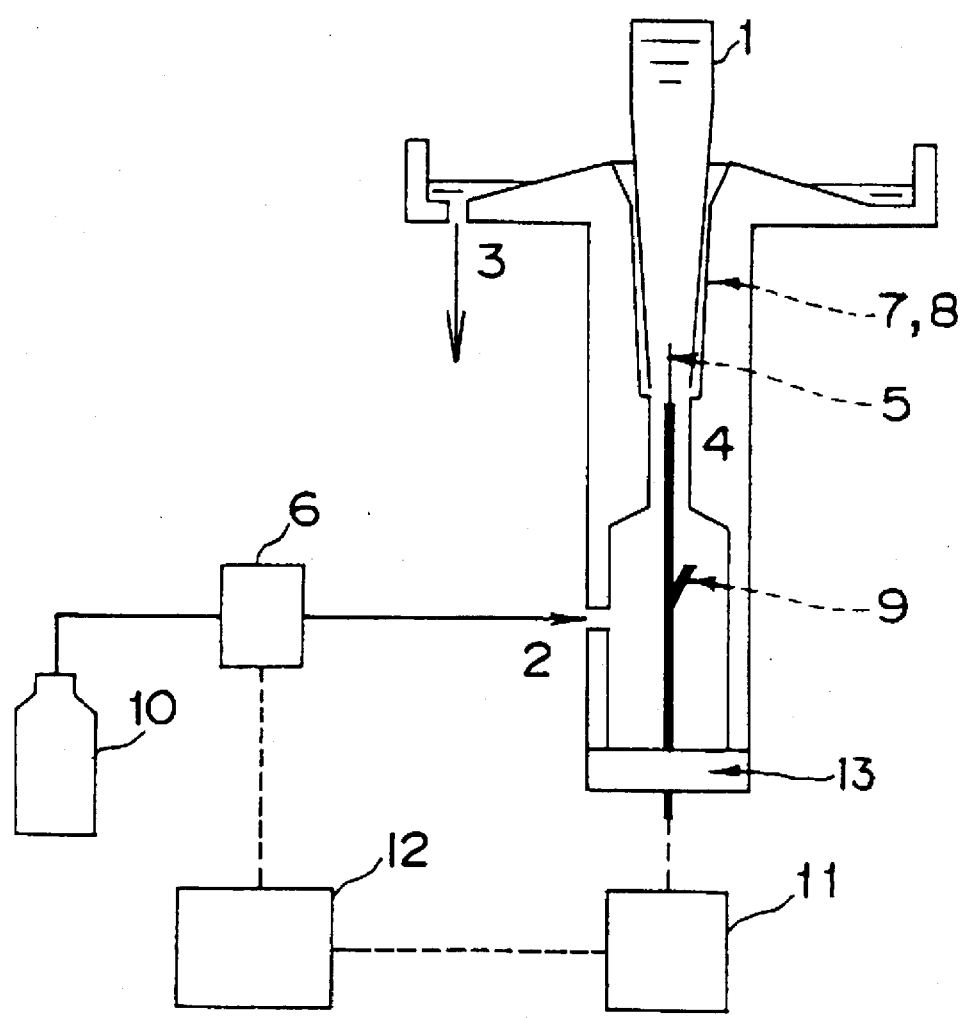
FIG. 2 is a schematic illustration showing a second embodiment of the apparatus of the present invention.

FIG. 2 shows the second embodiment of the present invention.

In FIG. 2, since the upper large diameter portion 7 of the cuvette 4 functions as a guide for the small diameter tube 1, the portion plays a role as a means for positioning the small diameter tube 1. In addition, due to the taper-like structure, the portion plays a role as a sealing means for maintaining a space formed by the outer surface of the small diameter tube 1 and the inner surface of the cuvette 4 at a liquid tight condition. The taper-like structure of the upper large diameter portion of the cuvette 4 is practical and preferable because a single means can serve not only as a means for positioning the small diameter tube 1 but also as a sealing means. In addition, since other constructions are the same as those of the first embodiment in FIG. 1, the explanation thereof is omitted and instead the same or corresponding part is displayed by attaching the same symbol thereto.

In the above embodiments, the small diameter tube 1 is inserted through the upper part of the cuvette 4. However, the small diameter tube 1 can be inserted through the side or lower part of the cuvette by appropriately modifying the shape of the cuvette 4.

The following experiments are explained in order to make clear the effects of the present apparatus.

Experiment 1 (Determination of urease)

A. Construction of the apparatus for determination

An apparatus shown in FIG. 1 was constructed. As a pH electrode 5, a pH electrode obtained by depositing a tantalum oxide as a pH sensitive membrane on the gate part of an entirely cicumferentially-insulated type pH-FET prepared according to the method described in JP-B 57-43863 was used. This pH-FET has a 5.5 mm length a width of 0.45 mm and a thickness of 0.15 mm, and the tip thereof having a length of about 0.8 mm is provided with the gate part (pH sensitive plane). This pH-FET was exposed in the cuvette by the tip, which contains the gate part, having the length of about 1.5 mm and the remainder was insulated with a resin. A small diameter tube was made of a polypropylene tube having a inner diameter of 0.55 mm, an outer diameter of 1.0 mm and a length of 30 mm. The upper large diameter portion 7 of the cuvette 4 was designed so that the pH-FET is accommodated in the center of the inner diameter of the small diameter tube 1. In this case, the maximum gap between the pH sensitive plane of the pH-FET and the inner surface of the small diameter tube 1 was (0.55−0.15)/2=0.20 mm. As a sealing means 8, an O ring having the inner diameter of 1 mm was used. As a reference electrode 9, a silver/silver chloride type liquid-junction reference electrode was provided in the lower large diameter portion of the cuvette 4. As the pump 6, a perista pump was used and the supplying rate was set at 0.5 ml/min.

The pH sensitivity of the pH-FET employed was 58 mV/pH at 25° C. and the mutual conductance was 350 microgiemens. The pH-FET was acted at the drain voltage of 4 volts and the drain current of 100 μA by connecting to the constant-current source. As an output signal of the pH-FET, the potential (referred to as "source potential" hereinafter) of the source of the pH-FET was measured using a reference electrode 9 as a standard.

B. Immobilization of anti-urease antibody to small diameter tube

Anti-urease antibody (manufactured by Sigma, mouse monoclonal antibody having soybean-derived urease as an immunogen, Clone UR-25) was selected as a receptor for urease and immobilized to the above small diameter tube 1 as follows. A PBS solution (pH 7.4) containing 100 μg/ml of the above anti-urease antibody was prepared, 1 μl of the solution was poured in the tip part of the above polypropylene tube using a micropipette, and then an anti-urease antibody was immobilized on the inner surface of the tip part of the tube by allowing it to stand at room temperature for 24 hours in a humidity retaining box. A PBS solution containing anti-urease antibody which remained unimmobilized in the tip part of the tube was removed by absorption with a paper towel, the tube was soaked in a PBS solution (pH 7.4) containing 10% sucrose, 1% bovine serum albumin and 0.1% sodium azide, and a blocking treatment was carried out by allowing it to stand at 4° C. for 24 hours.

C. Determination of urease

Figure 4:
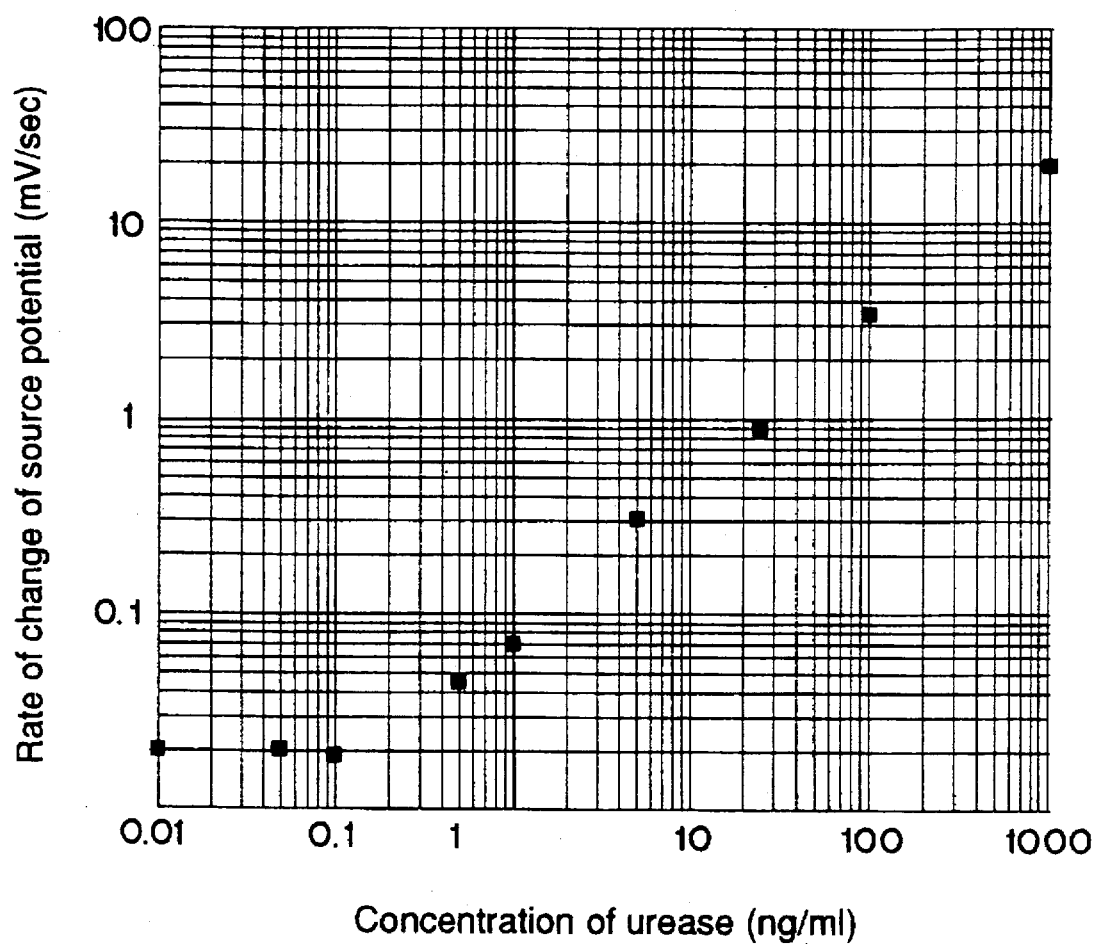
FIG. 4 is a graph showing the relation between the concentration of urease and the rate of change in source potential.

As urease, soybean-derived urease (manufactured by Sigma, U376) was used. The urease was dissolved at a predetermined concentration in a PBS solution (pH 7.4) containing 1% bovine serum albumin, 1 mM EDTA and 0.1% sodium azide and the resulting solution was used as a sample solution. 1 μl of the sample solution was sucked in the small diameter tube 1 having an immobilized anti-urease antibody on its inner surface (obtained in Experiment 1, B), and urease was captured on the inner surface of the small diameter tube 1 by allowing it to stand at room temperature for 10 minutes. As a substrate solution, a PBS solution containing 155 mM urea, 10 mM ammonium chloride and 154 mM sodium chloride was used. The small diameter tube 1 having captured urease on its inner surface was inserted in the cuvette 4 as shown in FIG. 3 while supplying the substrate solution in the cuvette 4 using a perista pump 6, and the interior of the small diameter tube 1 was washed for 30 seconds. Thereafter, the perista pump 6 was stopped and, from that point, a change in the source potential was measured for 10 seconds to obtain the rate of the change by the least square method. After the measurement was completed, the above small diameter tube 1 was pulled out from the cuvette 4, a substrate solution was supplied for 20 seconds in the cuvette 4 by driving the perista pump 6 to wash the cuvette 4 for the next measurement. The measurement results are shown in FIG. 4. Apparent from FIG. 4, 0.5 ng/ml of urease in 1 μl of a sample solution (about $8\times10^{-13}$M urease presuming that molecular weight of urease is 560 thousands) can be detected. That is, $8\times10^{-19}$ mole of an absolute amount of urease can be detected.

Experiment 2 (Determination of Lyt-2 positive subset in mouse T lymphocyte)

A. Immobilization of anti-mouse Lyt-2, 1 antibody on the small diameter tube

As a receptor for mouse Lyt-2 positive T cell, anti-mouse Lyt-2, 1 antibody (manufactured by COSMOBIO, Clone 49-31, 1) was used. A PBS solution (pH 7.4) containing 10 μg/ml of anti-mouse Lyt-2, 1 antibody was prepared. 1 μl of the solution was used to immobilize anti-mouse Lyt-2, 1 antibody on the inner surface of the tip part of the same polypropylene tube as used in Experiment 1 according to the same manner as that in Experiment 1, B. Then, a blocking treatment was carried out according to the same manner as that in Experiment 1, B.

B. Isolation and culturing of mouse Lyt-2 positive and negative T cell 3 ml of a PBS solution (pH 7.2) containing 50 μg/ml of goat anti-mouse Ig antibody (manufactured by Cappel) was placed in a plastic Petri dish (manufactured by Falcon, #3002) having a diameter of 6 cm, and then the goat anti-mouse Ig antibody was adsorbed on the Petri dish by allowing it to stand at 4° C. for 24 hours. $3\times10^{7}$ of cells of a lymphocyte fraction isolated from mouse spleen by normal specific gravity centrifugation were suspended in 3 ml of 5% FCS-RPMI-1640 (Medium, manufactured by GIBCO, #320-1895PK), were wound in one Petri dish having the adsorbed goat anti-mouse Ig antibody described above and allowed to stand at room temperature for 30 minutes. The Petri dish was swung gently to suspend the cells therein, allowed to stand at room temperature for 30 minutes, cells were resuspended according to the above method and the mouse lymphocyte T cell was isolated by recovering the resuspended cells.

Then, according to the same manner as that described above, a PBS solution containing 50 μg/ml of anti-mouse Lyt-2, 1 antibody (manufactured by COSMOBIO, Clone 49-31, 1) was used to adsorb anti-mouse Lyt-2, 1 antibody on a plastic Petri dish. $3\times10^{7}$ cells of the mouse lymphocyte T cell isolated by the same manner as that described above were suspended in 3 ml of 5% FCS-RPMI-1640 (Medium), were wound in one Petri dish having the adsorbed anti-mouse Lyt-2, 1 antibody described above and allowed to stand at 4° C. for 30 minutes. The cells were suspended by gently swinging the Petri dish, allowed to stand at 4° C. for 30 minutes, the cells were resuspended according to the same manner as that described above, and the cells (referred to as "Lyt-2 negative T cell) which do not bind to the suspended anti-mouse Lyt-2, 1 antibody were recovered. Then, the Petri dish from which a Lyt-2 negative cell had been recovered was washed four times with 5% FCS-RPMI-1640 (Medium), 5% FCS-RPMI-1640 (Medium) was added to the Petri dish, and vigorous pipetting was carried out to recover the cells (referred to as "Lyt-2 positive T cell" hereinafter) which bind to an anti-mouse Lyt-2, 1 antibody.

C. Determination of mouse Lyt-2 positive T cell

Figure 5:
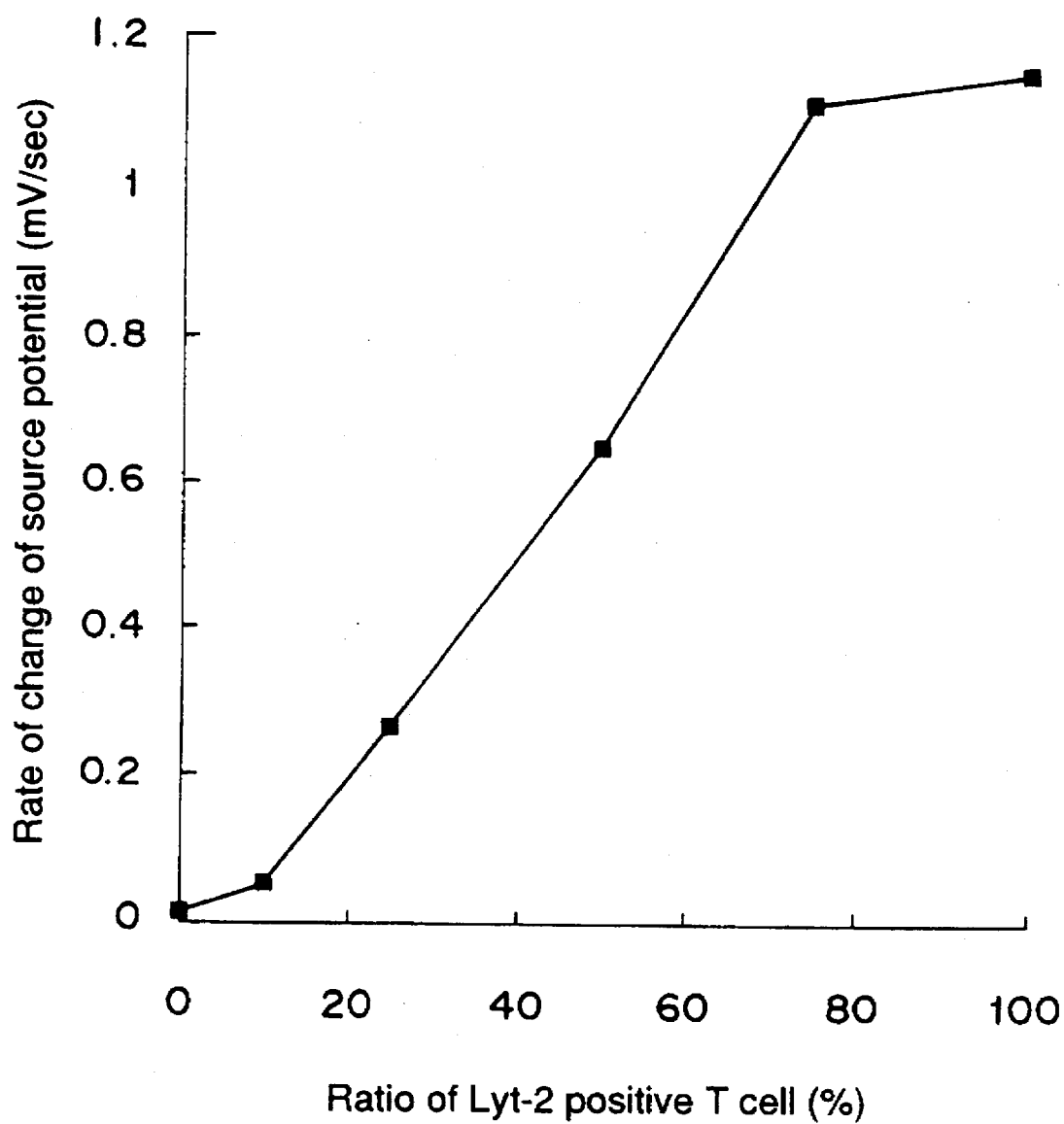
FIG. 5 is a graph showing the relation between the ratio of Lyt-2 positive T cell and the rate of change in the source potential.

Determination of a Lyt-2 positive T cell was carried out using the same apparatus as in Experiment 1. Six sample solutions, each containing $10^{7}$ cells of mouse lymphocyte T cell per 1 ml and having the ratio of Lyt-2 positive T cell of 0, 10, 25, 50, 75 or 100%, respectively, were prepared by suspending Lyt-2 positive T cell and Lyt-2 negative T cell isolated above (Experiment 2, B) in 5% FCS-RPMI-1640 (Medium). Each 1 μl of the above sample solutions was sucked in the small diameter tube 1 having, on its inner surface, the immobilized anti-mouse Lyt-2, 1 antibody obtained above (Experiment 2, A), and a Lyt-2 positive T cell was captured on the inner surface of the small diameter tube 1 by allowing it to stand at room temperature for 20 minutes. As a substrate solution, a PBS solution containing 10 mM ammonium chloride, 1 mM potassium bicarbonate, 1 mM EDTA, 0.5% glucose and 154 mM sodium chloride was prepared. The small diameter tube 1 having, on its inner surface, the captured Lyt-2 positive T cell was inserted in the cuvette 4 as shown in FIG. 3 while supplying a substrate solution in the cuvette 4 using a perista pump 6 to wash the interior of the small diameter tube 1 for 30 seconds. Thereafter, the perista pump 6 was stopped and, from that point, a change in the source potential for 60 seconds was measured. After the measurement was completed, the small diameter tube 1 was pulled out from the cuvette 4, the perista pump 6 was driven for 40 seconds to supply a substrate solution in the cuvette 4 to wash the cuvette 4 for the next measurement. The measurement results are shown in FIG. 5. As is apparent from FIG. 5, the Lyt-2 positive T cell can be selectively determined using the present apparatus.

What is claimed is:

1. An apparatus for the determination of a trace amount of an analyte substance or organism by bringing a substrate solution into contact with a small diameter tube, wherein a specific binding substance specific for the analyte substance or organism is immobilized at least on an inner surface of the small diameter tube, with the trace amount being captured by the binding substance, at least on the inner surface of the small diameter tube, the trace amount having the ability to change the pH of the substrate solution, and by measuring a pH change following a reaction of a substrate in the substrate solution in the small diameter tube, which apparatus comprises:

a cuvette having an inlet and an outlet for the substrate solution;

the small diameter tube having a lower opening for receiving a substrate solution from said cuvette and an upper opening through which the substrate solution passes out of said small diameter tube and into said cuvette;

a pH electrode accommodated in said cuvette, said pH electrode defining a pH sensitive plane;

pumping means for supplying the substrate solution to said cuvette;

positioning means for positioning in said cuvette, the small diameter tube which has captured, at least on its inner surface, the specific binding substance specific for the analyte substance or organism, to be determined so as to confront the inner surface of the small diameter tube with the pH sensitive plane of said pH electrode and space said inner surface and said pH sensitive plane at 1 mm or less from each other; and sealing means for maintaining a space formed by the outer surface of the small diameter tube accommodated in said cuvette and the inner surface of said cuvette at a liquid tight condition.

2. The apparatus according to claim 1, wherein said pH electrode is a pH sensitive field-effect transistor.

3. The apparatus according to claim 1, wherein said cuvette has large diameter portions at its upper and lower part and a small diameter portion at its intermediate part, both ends of the large diameter portions are open, and the upper large diameter portion is tapered such that its size descends towards the intermediate part.

* * * * *

UNITED STATES PATENT AND TRADEMARK OFFICE
CERTIFICATE OF CORRECTION

PATENT NO. : 5,674,696
DATED : October 7, 1997
INVENTOR(S) : Michihiro Nakamura et al It is certified that error appears in the above-indentified patent and that said Letters Patent is hereby corrected as shown below:

Claim 1, column 11, line 27, "an" should be "the".

Signed and Sealed this

Thirty-first Day of March, 1998

Attest:

BRUCE LEHMAN

Attesting Officer     Commissioner of Patents and Trademarks